(12) United States Patent
Paine

(10) Patent No.: US 10,751,167 B2
(45) Date of Patent: Aug. 25, 2020

(54) ACCOMMODATING INTRAOCULAR LENS SYSTEMS AND INTRAOCULAR LENS FOCUSERS

(71) Applicant: Timothy Paine, Westhay (GB)

(72) Inventor: Timothy Paine, Westhay (GB)

(*) Notice: Subject to any disclaimer, the term of this patent is extended or adjusted under 35 U.S.C. 154(b) by 102 days.

(21) Appl. No.: 15/525,289

(22) PCT Filed: Nov. 9, 2015

(86) PCT No.: PCT/GB2015/053384
§ 371 (c)(1),
(2) Date: May 8, 2017

(87) PCT Pub. No.: WO2016/071717
PCT Pub. Date: May 12, 2016

(65) Prior Publication Data
US 2017/0312070 A1    Nov. 2, 2017

(30) Foreign Application Priority Data
Nov. 7, 2014 (GB) .................................. 1419905.3

(51) Int. Cl.
*A61F 2/16* (2006.01)

(52) U.S. Cl.
CPC .......... *A61F 2/1616* (2013.01); *A61F 2/1624* (2013.01); *A61F 2/1629* (2013.01);
(Continued)

(58) Field of Classification Search
CPC .... A61F 2/1616; A61F 2/1624; A61F 2/1629; A61F 2002/1681; A61F 2002/1682;
(Continued)

(56) References Cited

U.S. PATENT DOCUMENTS

| 4,403,354 A | 9/1983 | Rainin |
|---|---|---|
| 6,299,641 B1 | 10/2001 | Woods |

(Continued)

FOREIGN PATENT DOCUMENTS

| DE | 10125829 A1 | 11/2002 |
|---|---|---|
| EP | 2412337 A1 | 2/2012 |

(Continued)

OTHER PUBLICATIONS

IOLs: surgical presbyopia developments; Jul. 23, 2013; Sheppard et al.

*Primary Examiner* — David H Willse
*Assistant Examiner* — Tiffany P Shipmon
(74) *Attorney, Agent, or Firm* — Will Hunziker

(57) ABSTRACT

An intraocular lens focuser (114) to be implanted in a human eye includes a resiliently deformable force applicator (140) to apply a focussing force to an accommodating intraocular lens and an attaching portion configured to enable attachment of the lens focuser in the eye. The force applicator is configured such that, in use, when a ciliary muscle of the eye is relaxed to place the accommodating intraocular lens in a distance vision condition, the force applicator is in a deformed condition and when the ciliary muscle contracts to place the accommodating intraocular lens in a near vision condition the force applicator resiles towards a relaxed non-deformed condition to at least assist in placing the accommodating intraocular lens in the near vision condition. The attaching portion has a plurality of members configured to permit attachment of the force applicator to at least one of i) an exterior of a capsular sac of the eye ii) zonules of the eye and iii) the ciliary muscle with the force applicator disposed exteriorly of the capsular sac.

13 Claims, 6 Drawing Sheets

(52) U.S. Cl.
CPC . *A61F 2002/169* (2015.04); *A61F 2002/1681* (2013.01); *A61F 2002/1682* (2015.04); *A61F 2220/0008* (2013.01); *A61F 2220/0025* (2013.01); *A61F 2230/0006* (2013.01)

(58) Field of Classification Search
CPC .... A61F 2002/1686; A61F 2002/16902; A61F 2002/1683; A61F 2002/16905; A61F 2002/16903; A61F 2220/0025; A61F 2220/0008; A61F 2230/0006
See application file for complete search history.

(56) References Cited

U.S. PATENT DOCUMENTS

| | | |
|---|---|---|
| 2001/0021831 A1 | 9/2001 | Fleischhacker et al. |
| 2003/0050695 A1 | 3/2003 | Lin |
| 2005/0113914 A1 | 1/2005 | Miller et al. |
| 2006/0047339 A1 | 3/2006 | Brown |
| 2007/0021831 A1 | 1/2007 | Clarke |
| 2007/0088433 A1 | 4/2007 | Esch |
| 2010/0204787 A1 | 8/2010 | Noy |
| 2011/0082544 A1 | 4/2011 | Nulens |
| 2012/0078363 A1 | 3/2012 | Lu |
| 2012/0253459 A1* | 10/2012 | Reich ............... A61F 2/1635 623/6.46 |
| 2013/0190868 A1 | 7/2013 | Kahook et al. |
| 2013/0304204 A1 | 7/2013 | Bumbalough et al. |
| 2014/0121768 A1 | 5/2014 | Simpson |

FOREIGN PATENT DOCUMENTS

| | | |
|---|---|---|
| GB | 2518378 A1 | 3/2015 |
| WO | WO2011062826 A2 | 5/2011 |

* cited by examiner

ACCOMMODATING INTRAOCULAR LENS SYSTEMS AND INTRAOCULAR LENS FOCUSERS

CROSS REFERENCE TO RELATED APPLICATIONS

This application claims the benefit of PCT patent application #: PCT/GB2015/053384, Filed Nov. 9, 2015 titled "Accommodating Intraocular Lens Systems And Intraocular Lens Focusers", which claims the benefit of Great Patent Application No. GB1419905.3, filed on Nov. 7, 2014, and titled "Accommodating Intraocular Lens Systems And Intraocular Lens Focuser" which is incorporated by reference herein in its entirety for all purposes.

FIELD OF THE INVENTION

The invention relates to accommodating intraocular lens systems and intraocular lens focusers for use in accommodating intraocular lens systems.

BACKGROUND TO THE INVENTION

The lens of the human eye is originally flexible and focuses for vision at different distances by deforming so as to change its thickness in the axial direction of the eye. For near vision the lens is relatively fat, or thick, and for distance vision it is stretched so that it becomes relatively thin. The lens cannot have a blood supply and consequently with age will tend to become stiffer and misty. As the lens becomes stiffer, the range of clear vision is reduced. This is why older people often require reading spectacles, bifocals or varifocals. The mistiness is cataract.

For the treatment of cataracts it is known to perform a surgical procedure in which the cataracted lens is removed from the eyeball through a small incision made in the wall of the cornea and replaced by an artificial intraocular lens. One known surgical procedure involves the extracapsular removal of the cataracted natural lens, leaving portions of the lens sac, or capsular sac, intact to hold the implanted intraocular lens. The intraocular lens is folded and inserted into the capsular sac where it unfolds. The intraocular lens has two side struts called haptics that press against the inner side of the capsular sac to hold the lens in place within the capsular sac.

SUMMARY OF THE INVENTION

The invention provides an intraocular lens focuser as specified in claim 1.

The invention also includes an accommodating intraocular lens system as specified in claim 15.

BRIEF DESCRIPTION OF THE DRAWINGS

In the disclosure that follows, reference will be made to the drawings in which.

DETAILED DESCRIPTION

Figure 1:
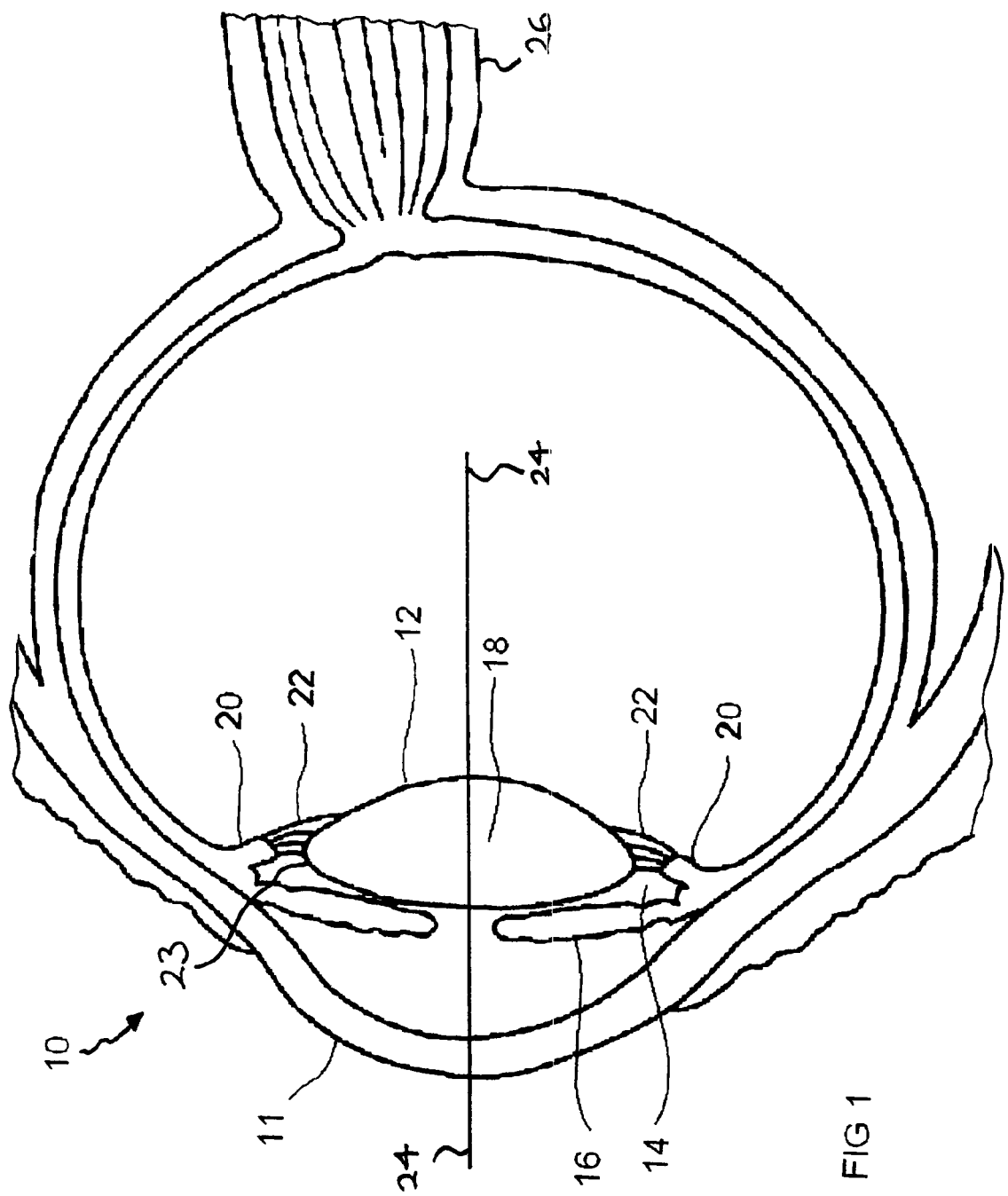
FIG. 1 is a schematic side section view of a human eye.

Referring to FIG. 1, a human eye 10 comprises a cornea 11 and a lens sac, or capsular sac, 12 disposed in a posterior chamber 14 that is disposed posteriorly, or inwardly, of the iris 16. The capsular sac 12 contains a crystalline lens 18 and is connected with ciliary muscle 20 by zonules 22. The zonules 22 are attached to the outer periphery of the capsular sac at an equatorial region 23 of the sac that corresponds generally to the major diameter of the sac. The ciliary muscle 20 can move between a contracted condition (shown in FIG. 1) in which the lens 18 is relatively fat for near vision and a relaxed condition which causes the lens to be pulled to make it relatively thin for distance vision. Specifically, in the contracted position shown in FIG. 1, the lens 18 is relatively fat, or thick, in the axial direction through the centre of the eye that is indicated by line, or principal axis, 24 and when the lens is pulled by the relaxation of the ciliary muscle, that thickness is reduced.

Figure 2:
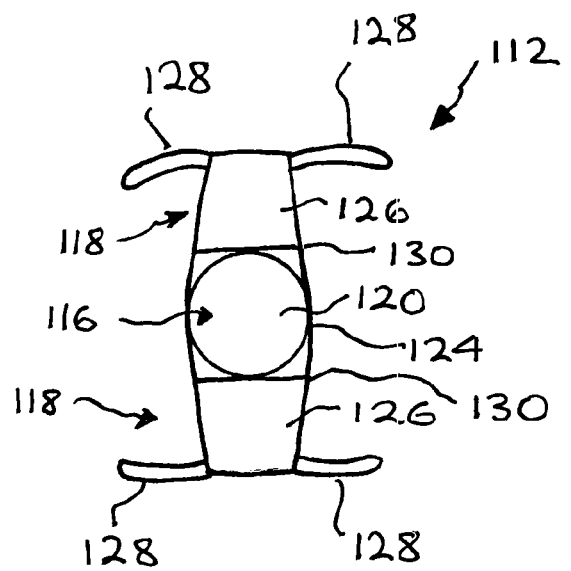
FIG. 2 is a schematic front elevation view of an example of an accommodating intraocular lens system in a disassembled condition.
Figure 2:
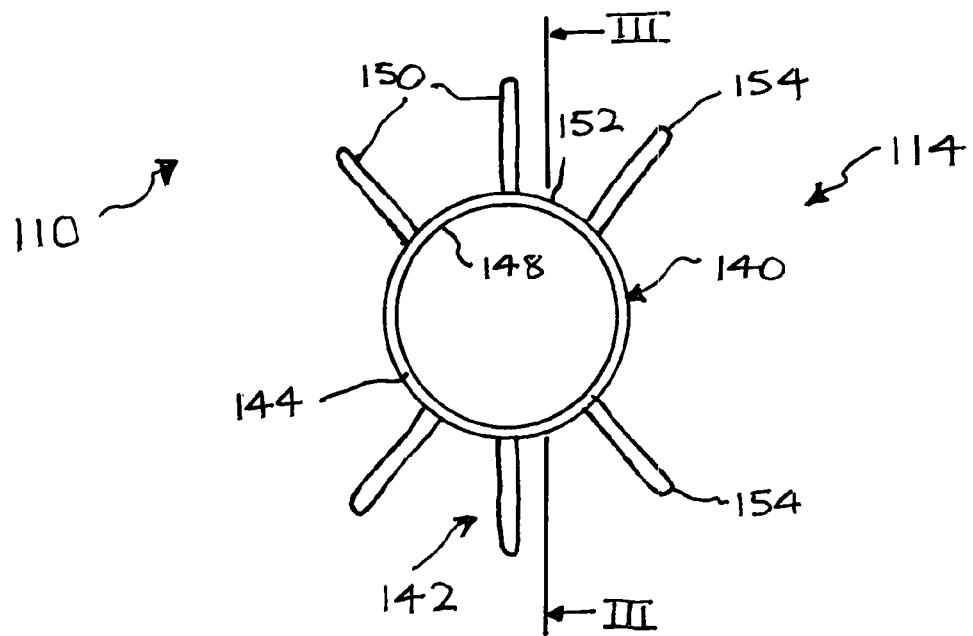
Figure 3:
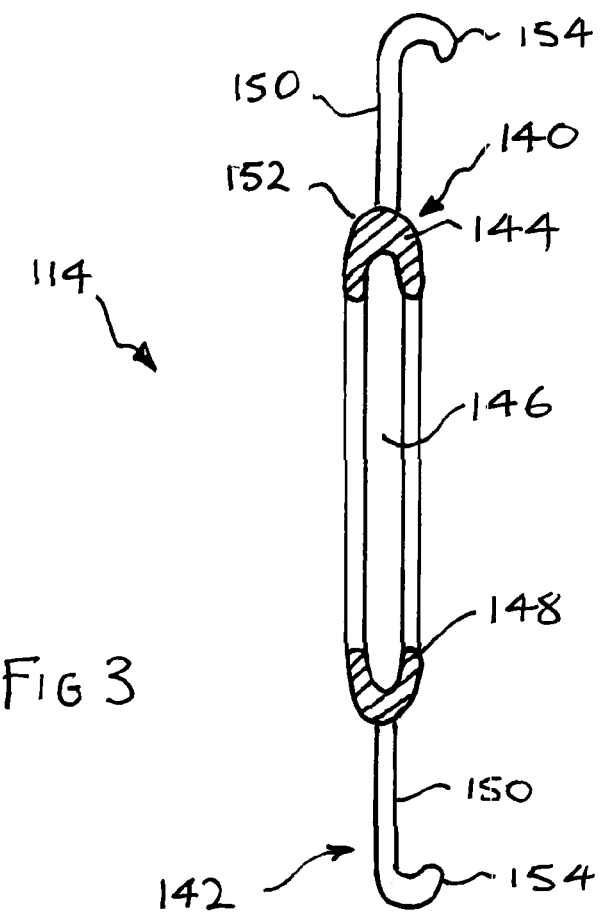
FIG. 3 is a section view on line in FIG. 2 showing an intraocular lens focuser of the accommodating intraocular lens system.
Figure 4:
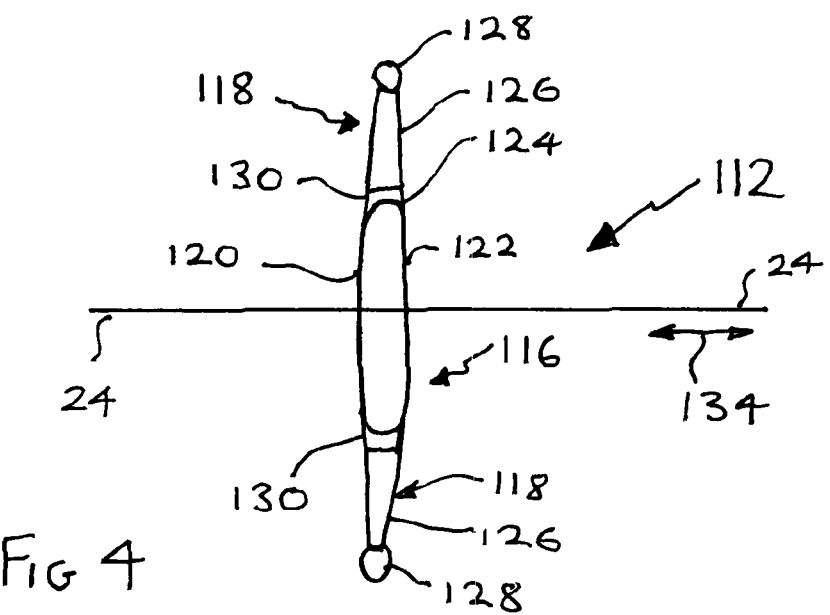
FIG. 4 is a side elevation view of an accommodating intraocular lens of the accommodating intraocular lens system of FIG. 2.

Referring to FIGS. 2 to 4, an accommodating intraocular lens system 110 comprises an accommodating intraocular lens (AIOL) 112 and an intraocular lens focuser 114. The AIOL 112 comprises a lens body 116 and a haptic portion 118. The lens body 116 has an anterior side 120, a posterior side 122 and an outer periphery 124. In this example the haptic portion 118 comprises diametrically opposed arms 126 extending from the outer periphery 124 of the lens body 116 and resilient fingers 128 projecting from the free end of each arm 126. The haptic portion 118 is configured to define respective hinges 130 between the radially inner ends of the arms 126 and the outer periphery 124 of the lens body 116 so that, in use, the lens body can move back and forth in the axial direction of the eye, as indicated by the arrow 134 in FIG. 4, the hinges 130 may be defined by selective thinning of the arms 126 in respective regions adjacent the respective positions at which they join the lens body, or by providing a more resilient material between the arms and the lens body.

The intraocular lens focuser 114 comprises a resiliently deformable force applicator 140 and an attaching portion 142 configured to enable attachment of the lens focuser to the eye.

The force applicator 140 is configured to apply a generally radially inwardly directed focus adjusting force to the AIOL 112 and in this example comprises an annular body 144. The annular body 144 may be a generally planar body as illustrated in FIG. 3. The annular body 144 comprises at least one holding formation 146 (FIG. 3) engagable by the AIOL 112 to hold the AIOL in the eye. In the illustrated example, the holding formation is a circumferentially extending groove 146 that extends at least substantially continuously around the inner periphery 148 of the annular body 144. The resilience of the annular body 144 is such that the haptic portion 118 of the AIOL 112 is able to engage with the groove 146 by push-fitting. In the illustrated example, the free ends of the arms 126 can be inserted in the groove 146.

The attaching portion 142 of the intraocular lens focuser 114 comprises a plurality of formations 150 disposed at spaced apart intervals about the outer periphery 152 of the force applicator 140. In the illustrated example the formations comprise a plurality of arms 150 that project outwardly of the outer periphery 152 of the force applicator 140. The arms 150 may lie generally in the plane of the force applicator 140 or may be inclined with respect to the plane of the force applicator. The free ends 154 of the arms 150 are hooked to permit the intraocular lens focuser 114 to be attached to the eye by hooking onto the capsular sac 12 or the zonules 22. The arms 150 are made stiffer than the force applicator 140 so that in use when the force applicator is deformed by contraction of the ciliary muscle 20, the arms remain at least substantially non-deformed so that at least a significant portion of the full range of movement of the ciliary muscle is applied to deforming the force applicator 140. The force applicator 140 may be made of a suitably resilient material such as a surgically approved silicon and the arms 150 made of a less resilient material. The intraocular lens focuser 114 may be formed by co-moulding the force applicator 140 and the attaching portion 142.

The fitting of the accommodating intraocular lens system 100 in a human eye 10 will now be described with reference to FIGS. 1 and 5. First, the lens 18 is removed by a surgical procedure known as phacoemulsification. This involves making a small incision in the cornea 11 through which a tool is inserted to remove a portion of the anterior side of the capsular sac 12. Then a tool is inserted into the capsular sac 12 to break up and emulsify the lens 18 by means of ultrasonics, following which the lens is removed using a suction tool. Once the lens 18 is completely cleaned from the capsular sac 12, the accommodating intraocular lens system 110 is implanted in the eye 10.

The first stage of implanting the accommodating intraocular lens system 110 comprises inserting the intraocular lens focuser 114 into the eye through the incision in the cornea 11. The incision may need to be widened to allow insertion of the intraocular lens focuser 114. The intraocular lens focuser 114 is attached to the eye by systematically hooking the free ends 154 of the arms 150 over the periphery of the capsular sac 12 and through the zonules 22 at, or near, the equatorial region 23. This process gradually deforms the force applicator 140 so that when fitted to the capsular sac 12 it is in a deformed, or stretched, condition configured for a distance vision condition of the accommodating intraocular lens system 110. Once the intraocular lens focuser 114 has been properly attached to the capsular sac 12, the AIOL 112 is fitted to the force applicator 140 by push-fitting the free ends of the arms 126 and the resilient fingers 128 into the groove 146. At this stage, the intraocular lens focuser 114 and AIOL 112 are configured for distance vision with the lens body 116 disposed in a relatively posterior position in the eye 10. It can be seen that the AIOL 112 and intraocular lens focuser 114 are disposed in the anterior chamber 14 in front of and generally exterior to the capsular sac 12.

Figure 5:
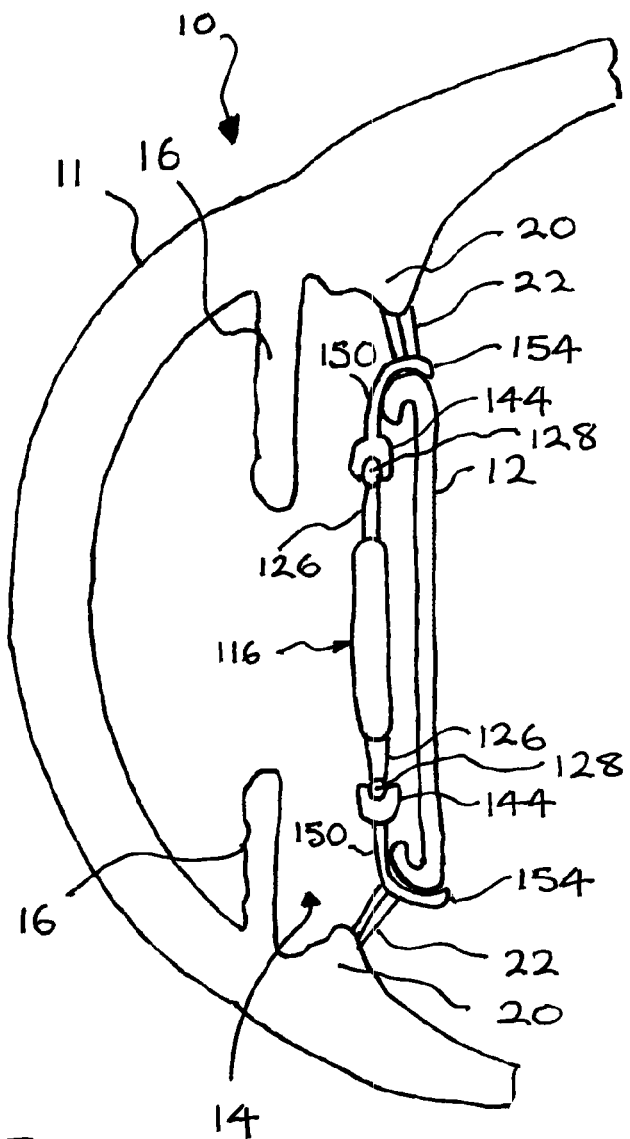
FIG. 5 is a schematic side view of the accommodating intraocular lens system of FIG. 2 implanted in a human eye.
Figures 6, 7:
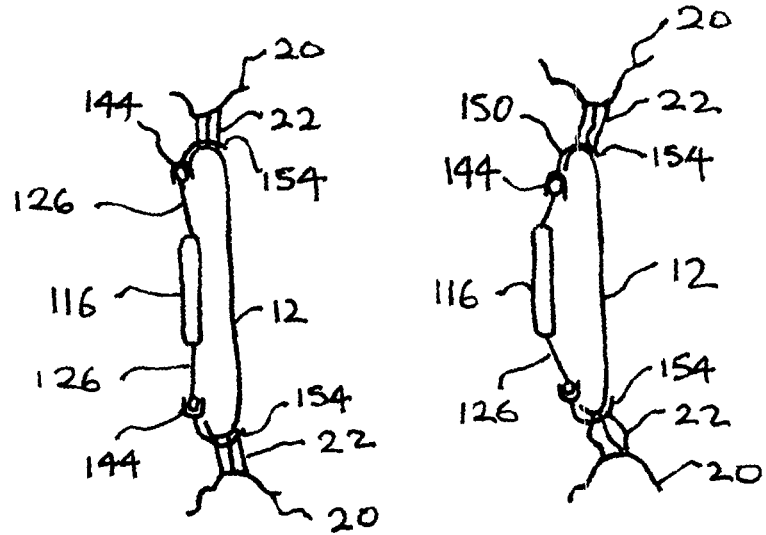
FIGS. 6 and 7 are schematic representations of the accommodating intraocular lens implant of FIG. 5 showing focussing movement of the accommodating intraocular lens.

FIG. 6 is a view corresponding generally to FIG. 5. The ciliary muscle 20 is relaxed so that the zonules 22 are pulled relatively tight. The tightness of the zonules 22 is transferred to the force applicator 140 of the intraocular lens focuser 114 via the capsular sac 12. The tautness of the zonules 22 causes the annular body 144 of the force applicator 140 to adopt a deformed, stretched, condition that allows the AIOL 12 to adopt a posteriorly vaulted condition so that lens body 116 is disposed relatively posteriorly in the eye 10 thereby configuring the accommodating intraocular lens system 110 for distance vision. In FIG. 7, the ciliary muscle 20 has contracted for near vision resulting in a relaxation of the zonules 22. The relaxation of the zonules 22 releases the tension in the force applicator 140 and capsular sac 12. As the tension is released, the annular body 144 is able to resile to an undeformed condition. As the annular body 140 resiles to an undeformed condition, the release of energy stored in the annular body applies a focus adjusting force to the AIOL 112. The focus adjusting force at least assists in causing the lens body 116 to be shifted anteriorly by operation of the hinges 130 allowing relative movement between the arms 126 and lens body. With the lens body 116 disposed in a relatively anterior position as shown in FIG. 7, the accommodating intraocular lens system 110 is in a condition configured for near vision. When the ciliary muscle 20 is relaxed again for distance vision, the zonules 22 are again tightened, causing pulling on the capsular sac 12 and the arms 150 of the intraocular lens focuser 114. As the capsular sac 12 and annular body 144 are stretched by the pulling of the zonules 22, the generally radially inwardly acting focus adjusting force acting on the haptic portion 118 of the AIOL 112 is reduced so that the AIOL can relax, or resile, towards the condition shown in FIG. 6, returning the accommodating intraocular lens system 110 to a distance viewing condition.

Figure 8:
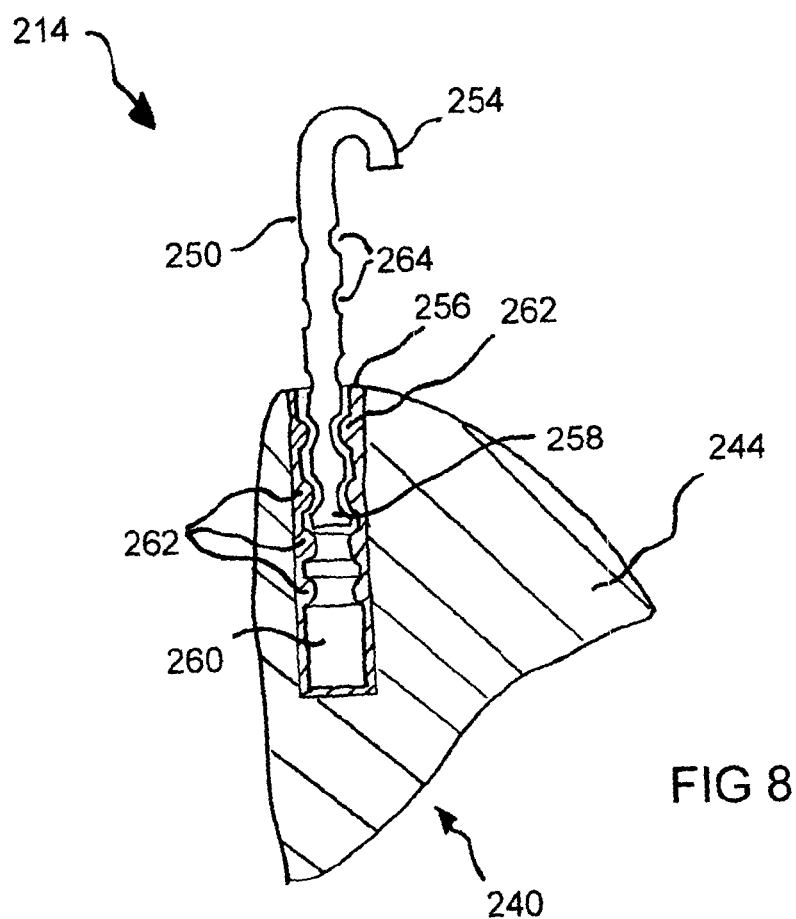
FIG. 8 is a schematic partial side view of the intraocular lens focuser of FIGS. 2 and 3 showing a modified attaching portion.

FIG. 8 shows a portion of a modified intraocular lens focuser 214, which differs from the lens focuser 114 shown in FIGS. 2 and 3 in that the arms 250 are length adjustable. In the description that follows, parts of the intraocular lens focuser 214 that are the same as, or similar to, parts of the intraocular lens focuser 114 will be given the same reference numerals, incremented by 100, and may not be described again.

The annular body 244 of the force applicator 240 is provided with respective tubes 256 to receive first ends 258 of the arms 250 (ie the ends opposite to the hooked free ends 254). The tubes 256 each define a passage 260 to receive the respective arms 250. The passages 260 may be a blind bores or through-holes. The passages 260 are provided with a plurality of formations 262. The formations 262 are arranged in a series along at least a portion of the length of the tubes 256. In the illustrated example, the formations 262 comprise a series of annular ribs disposed in spaced apart relation along the length of a passage 260. In the illustrated example, the formations 262 are generally semi-circular in cross-section, although any other suitable profile may be used. The arms 250 are provided with a series of formations 264 to interengage the formations 262 of the tubes 256. In the illustrated example, the formations 264 are annular depressions, or grooves, configured to mate with the formations 262 of the tubes 256.

The interengagement of the formations 262, 264 defines a series of length adjustment positions that make the arms 250 length adjustable. This arrangement permits the surgeon to adjust the tension of force applicator 240 and alter the fit of the intraocular lens focuser 214 to fit different sized eyes.

In the illustrated example, the formations 262 are projections that engage in depressions 264 provided in the arms 250. It will be appreciated that this is not essential and that the arms 250 may be provided with projections to engage in depressions provided in the tube. Furthermore, it is not essential that the projections or depressions are annular as shown in the illustrated example. The projections may extend around a relatively small part of the circumference of the arms/tubes to engage in depressions that similarly extend around a relatively small part of the circumference of the arms/tubes. In general it may be desirable that in the case of non-annular depressions, the depressions extend around a greater portion of the circumference than the projections they mate with in order to avoid alignment issues. In another example, the formations on the tubes and arms may be resilient tines that have a radial extent configured such that they overlap when the arms are inserted into their respective tubes. The interengaging tines would act in similar fashion to a ratchet mechanism in defining a series of length adjustment positions.

Figure 9:
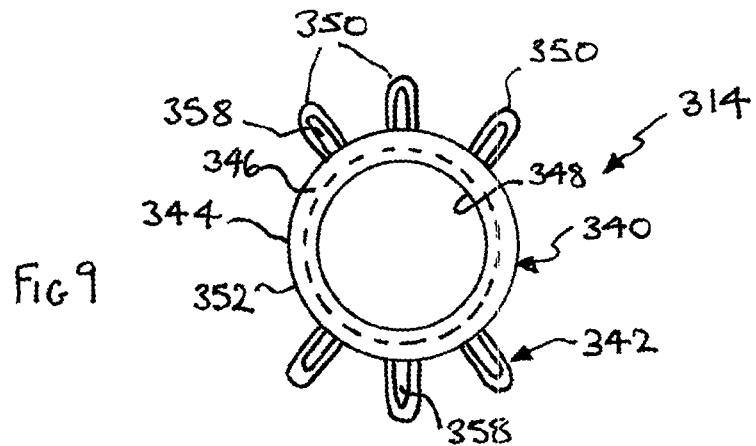
FIG. 9 is a schematic front elevation view of an alternative intraocular lens focuser.

FIG. 9 shows an alternative intraocular lens focuser 314 that can be used with an AIOL such as the AIOL 112. The intraocular lens focuser 314 comprises a force applicator 340 configured to apply a generally radially inwardly directed focus adjusting force to the AIOL 112 and an attaching portion 342 to be used in attaching the lens focuser to a human eye. In this example the force applicator 340 comprises an annular body 344, which may be a generally planar body similar to that shown in FIG. 3. Optionally, the annular body 344 comprises at least one holding formation 346 engagable by the AIOL 112 for holding the AIOL in the eye. In the illustrated example the holding formation is a circumferentially extending groove 346 that extends at least substantially continuously around the inner periphery 348 of the annular body 344. The resilience of the annular body 344 is such that the haptic portion 118 of the AIOL 112 is able to engage with the groove 346 by push-fitting.

The attaching portion 342 of the intraocular lens focuser 314 comprises a plurality of formations 350 disposed at spaced intervals about the outer periphery 352 of the force applicator 340. The formations 350 are configured to permit attachment to the eye by respective sutures. In the illustrated example the formations comprise respective loops 350, which may be generally U-shaped as shown. The loops 350 define respective apertures 358 through which a suture can pass. In other examples, the formations 350 may comprise ears projecting from the force applicator 340 or arms provided with one or more apertures that can receive a suture. The formations 350 may, for example, comprise arms projecting from the outer periphery of the force applicator 340 and provided with an enlargement at their free ends in which a suture receiving aperture is defined. The formations may be relatively short in the radially outward direction of the force applicator 340 so that the intraocular lens focuser 314 is configured for attaching to the capsular sac 12. Alternatively, the formations may be longer to configure the intraocular lens focuser 314 such that it can be sutured to the zonules 22 or, longer still for suturing to the ciliary muscle 20.

Figure 10:
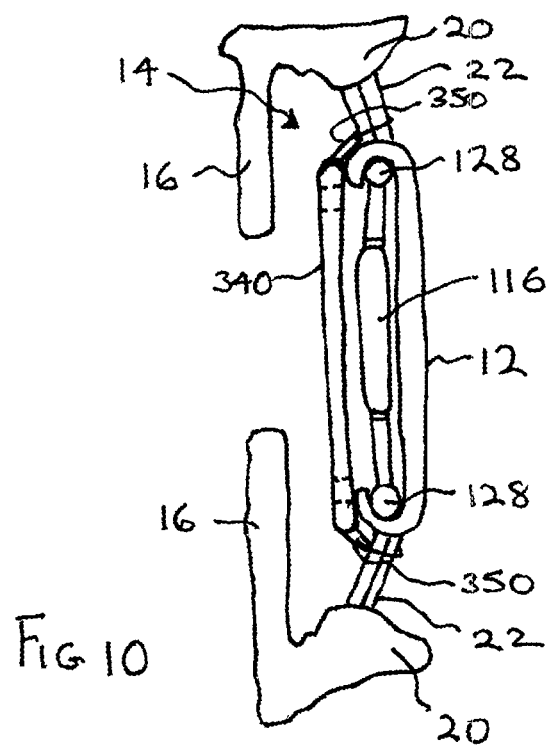
FIG. 10 is a schematic side view of an accommodating intraocular lens system including the intraocular lens focuser of FIG. 9 implanted in a human eye.

FIG. 10 shows an accommodating intraocular lens system comprising the AIOL 112 and the intraocular lens focuser 314 implanted in a human eye. In this example, the AIOL 112 has been fitted into the capsular sac 12 and the intraocular lens focuser 314 has been sutured to the zonules 22 by respective sutures 362 passing through the apertures 358 defined by the loops 350. It can be seen that in this example, while the intraocular lens focuser 314 is disposed anteriorly of the capsular sac in the posterior chamber 14, the AIOL 112 is disposed within the capsular sac 12. In another example, the AIOL may be fitted to the intraocular lens focuser 314 in similar fashion to that shown in FIG. 5 by engaging the resilient fingers 128 in the groove 346 of the annular body 344. In operation, the implant shown in FIG. 10 functions in analogous fashion to the implant shown in FIGS. 6 and 7 and so will not be described again.

It is believed an intraocular lens focuser operating according to the principles illustrated by the intraocular lens focusers 114, 314 can ensure the necessary movement of AIOLs that rely on generally anterior axial focussing movement of the lens body to provide adequate near vision for presbyopic eyes. It is believed that in many eyes, natural viewing of near stimulus results in relatively low levels of anterior movement of the lens body giving rise to an insufficient rise in the eye's refractive power. Movements of only 0.01 to 0.33 mm have been recorded in tests with AIOLs similar to the AIOL 112. It is believed an intraocular lens focusers as disclosed herein can induce a movement of at least 2.00 mm, which should be sufficient to give reasonable reading vision. A further benefit of the intraocular lens focuser is that if the capsular sac fibroses following the implant surgery, the focuser can ensure there is a sufficient focus adjusting force available to ensure the required anterior focussing movement of the lens body.

In the example shown in FIG. 5, the AIOL is fitted to the intraocular lens focuser exteriorly of the capsular sac, whereas in the example shown in FIG. 10, the AIOL is implanted in the capsular sac in a conventional manner. While it is not essential to configure the intraocular lens focuser to allow attachment of the AIOL and the AIOL may be implanted in the capsular sac as shown in FIG. 10, it may be desirable to have the facility to attach the AIOL to the focuser when insertion in the capsular sac is not possible, for example, in cases in which the capsular sac has ruptured.

In the illustrated example, the intraocular lens focuser is provided with a holding formation to hold an AIOL in a human eye in the form of a groove that extends at least substantially around the entire circumference of the force applicator body. It is to be understood that in some examples, the force applicator may be provided with a plurality of discrete holding formations disposed in suitably spaced apart relation. It is presently envisaged that an annular groove or the like as shown in the illustrated examples is advantageous in that orientating issues may be reduced.

In the illustrated example the holding formation comprises recessing into which parts of the haptic portion of the AIOL are fitted. In some examples, the intraocular lens focuser may be provided with one or more holding formations in the form of a projection that is engageable with a suitable formation provided on the haptic portion of the AIOL.

It is envisaged that the intraocular lens focuser concept may be used with AIOLs designed specifically for use with the focuser and with existing commercially available designs such as Bausch & Lomb's Crystalens® AIOL and Lenstec, Inc's Tetraflex AIOL.

The illustrated examples comprise an AIOL that provides focusing adjustment by movement of the lens body between anterior and posterior positions in the eye. In these examples the lens body remains at least substantially undeformed by such movement. In some examples, the focusing adjustment may be by deformation of the lens body, which is relatively thick in the direction of the principal axis 24 (FIG. 1) when the ciliary muscle is contracted for near vision focus and stretched relatively thinner when the ciliary muscle relaxes for distance vision. The intraocular lens focuser may be used with such AIOLs, which may be implanted in the capsular sac or fitted exteriorly of the sac as disclosed in the Applicant's co-pending United Kingdom Patent Application No 1316612.9, the content of which is incorporated herein by reference.

The invention claimed is:

1. An intraocular lens focuser to be implanted in a human eye, said lens focuser comprising a resiliently deformable force applicator to apply a focusing force to an accommodating intraocular lens and an attaching portion configured to enable attachment of the lens focuser in said eye,
   wherein said force applicator is configured such that, in use, when a ciliary muscle of said eye is relaxed to place said accommodating intraocular lens in a distance vision condition said force applicator is in a deformed condition and when the ciliary muscle contracts to place the accommodating intraocular lens in a near vision condition said force applicator resiles towards a relaxed non-deformed condition to at least assist in placing said accommodating intraocular lens in said near vision condition,
   wherein said attaching portion is configured to permit attachment of said force applicator to at least one of i) an exterior of a capsular sac of the eye, ii) zonules of the eye and iii) said ciliary muscle with said force applicator and said attaching portion disposed exteriorly of said capsular sac, and
   wherein said attaching portion comprises a plurality of spaced apart members and said members comprise arms that project from said force applicator and are configured to permit attachment by hooking.

2. An intraocular lens focuser as claimed in claim 1, wherein said arms are length adjustable.

3. An intraocular lens focuser as claimed in claim 1, wherein said attaching portion is configured to permit attachment of said force applicator such that said force applicator is disposed anteriorly with respect to said capsular sac.

4. An intraocular lens focuser as claimed in claim 1, wherein said force applicator is configured to apply a radially inwardly directed focusing force to said accommodating intraocular lens when resiling towards said relaxed non-deformed condition.

5. An intraocular lens focuser as claimed in claim 1, wherein said attaching portion is stiffer than said force applicator.

6. An intraocular lens focuser to be implanted in a human eye, said lens focuser comprising a resiliently deformable force applicator to apply a focusing force to an accommodating intraocular lens and an attaching portion configured to enable attachment of the lens focuser in said eye,
   wherein said force applicator is configured such that, in use, when a ciliary muscle of said eye is relaxed to place said accommodating intraocular lens in a distance vision condition said force applicator is in a deformed condition and when the ciliary muscle contracts to place the accommodating intraocular lens in a near vision condition said force applicator resiles towards a relaxed non-deformed condition to at least assist in placing said accommodating intraocular lens in said near vision condition,
   wherein said attaching portion is configured to permit attachment of said force applicator to at least one of i) an exterior of a capsular sac of the eye, ii) zonules of the eye and iii) said ciliary muscle with said force applicator and said attaching portion disposed exteriorly of said capsular sac, and
   wherein said attaching portion comprises a plurality of spaced apart members and said members comprise projections configured to permit attachment by respective sutures that engage said formations.

7. An intraocular lens focuser as claimed in claim 6, wherein said projections comprise respective loops.

8. An intraocular lens focuser to be implanted in a human eye, said lens focuser comprising a resiliently deformable force applicator to apply a focusing force to an accommodating intraocular lens and an attaching portion configured to enable attachment of the lens focuser in said eye,
   wherein said force applicator is configured such that, in use, when a ciliary muscle of said eye is relaxed to place said accommodating intraocular lens in a distance vision condition said force applicator is in a deformed condition and when the ciliary muscle contracts to place the accommodating intraocular lens in a near vision condition said force applicator resiles towards a relaxed non-deformed condition to at least assist in placing said accommodating intraocular lens in said near vision condition,
   wherein said attaching portion is configured to permit attachment of said force applicator to at least one of i) an exterior of a capsular sac of the eye, ii) zonules of the eye and iii) said ciliary muscle with said force applicator and said attaching portion disposed exteriorly of said capsular sac, and
   wherein said force applicator comprises an annular body.

9. An intraocular lens focuser to be implanted in a human eye, said lens focuser comprising a resiliently deformable force applicator to apply a focusing force to an accommodating intraocular lens and an attaching portion configured to enable attachment of the lens focuser in said eye,
   wherein said force applicator is configured such that, in use, when a ciliary muscle of said eye is relaxed to place said accommodating intraocular lens in a distance vision condition said force applicator is in a deformed condition and when the ciliary muscle contracts to place the accommodating intraocular lens in a near vision condition said force applicator resiles towards a relaxed non-deformed condition to at least assist in placing said accommodating intraocular lens in said near vision condition,
   wherein said attaching portion is configured to permit attachment of said force applicator to at least one of i) an exterior of a capsular sac of the eye, ii) zonules of the eye and iii) said ciliary muscle with said force applicator and said attaching portion disposed exteriorly of said capsular sac, and
   wherein said force applicator comprises at least one holding formation to be engagable by said accommodating intraocular lens for holding said accommodating intraocular lens in the eye.

10. An intraocular lens focuser as claimed in claim 9, wherein said at least one holding formation is configured to permit fitting of said accommodating intraocular lens to said force applicator by push-fitting.

11. An intraocular lens focuser as claimed in claim 9 or 10, wherein said at least one holding formation comprises at least one circumferentially extending groove.

12. An accommodating intraocular lens system to be implanted in a human eye, said accommodating intraocular lens system comprising:
   an accommodating intraocular lens comprising a lens body and a haptic portion; and
   an intraocular lens focuser comprising a force applicator and an attaching portion, wherein:
said lens body has a first condition defining a distance vision focus and a second condition defining a near vision focus and said haptic portion is configured to support said lens body such as to permit focusing adjustment of said lens body between said first and second conditions in response to relaxation and contraction of a ciliary muscle of said eye, said haptic portion is configured such that said focusing adjustment of said lens body comprises movement of said lens body between relatively anterior and posterior positions in said eye, said haptic portion comprises at least one hinge configured to permit said movement of the lens body, said attaching portion is configured to permit attachment of said force applicator to at least one of i) an exterior of a capsular sac of said eye, ii) zonules of said eye and iii) said ciliary muscle with said force applicator disposed exteriorly of said capsular sac, and said intraocular lens focuser is configured to deform, in use, in response to relaxation of said ciliary muscle and to resile towards a relaxed condition in response to contraction of said ciliary muscle, and said force applicator is configured to provide a focus adjusting force to least assist in focusing adjustment of said lens body to said second condition when said ciliary muscle contracts.

13. An accommodating intraocular lens system to be implanted in a human eye, said accommodating intraocular lens system comprising:

an accommodating intraocular lens comprising a lens body and a haptic portion; and an intraocular lens focuser comprising a force applicator and an attaching portion, wherein:
said lens body has a first condition defining a distance vision focus and a second condition defining a near vision focus and said haptic portion is configured to support said lens body such as to permit focusing adjustment of said lens body between said first and second conditions in response to relaxation and contraction of a ciliary muscle of said eye, said haptic portion comprises arms projecting from said lens body, said attaching portion is configured to permit attachment of said force applicator to at least one of i) an exterior of a capsular sac of said eye, ii) zonules of said eye and iii) said ciliary muscle with said force applicator disposed exteriorly of said capsular sac, said intraocular lens focuser is configured to deform, in use, in response to relaxation of said ciliary muscle and to resile towards a relaxed condition in response to contraction of said ciliary muscle, said force applicator is configured to provide a focus adjusting force to least assist in focusing adjustment of said lens body to said second condition when said ciliary muscle contracts, and said force applicator is configured to provide a focus adjusting force to least assist in focusing adjustment of said lens body to said second condition when said ciliary muscle contracts.

* * * * *